United States Patent
Libbus

(10) Patent No.: US 9,314,637 B2
(45) Date of Patent: Apr. 19, 2016

(54) METHOD AND APPARATUS FOR ELECTRONICALLY SWITCHING ELECTRODE CONFIGURATION

(71) Applicant: Cardiac Pacemakers, Inc., St. Paul, MN (US)

(72) Inventor: Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 98 days.

(21) Appl. No.: 13/647,260

(22) Filed: Oct. 8, 2012

(65) Prior Publication Data
US 2013/0030504 A1 Jan. 31, 2013

Related U.S. Application Data

(62) Division of application No. 11/130,023, filed on May 16, 2005, now abandoned.

(51) Int. Cl.
*A61N 1/36* (2006.01)
*A61N 1/372* (2006.01)
(Continued)

(52) U.S. Cl.
CPC ........ *A61N 1/37211* (2013.01); *A61N 1/36139* (2013.01); *A61N 1/36185* (2013.01); *A61N 1/362* (2013.01); *A61N 1/3688* (2013.01); *A61N 1/36114* (2013.01); *A61N 1/37235* (2013.01)

(58) Field of Classification Search
CPC ........... A61N 1/36128; A61N 1/36135; A61N 1/36139
See application file for complete search history.

(56) References Cited

U.S. PATENT DOCUMENTS

| 4,628,942 A | 12/1986 | Sweeney et al. |
| 4,920,979 A | 5/1990 | Bullara |

(Continued)

FOREIGN PATENT DOCUMENTS

| EP | 1304135 A2 | 4/2003 |
| JP | 2003522004 A | 7/2003 |

(Continued)

OTHER PUBLICATIONS

"U.S. Appl. No. 11/130,023, Decision on Appeal mailed Sep. 24, 2012", 7 pgs.

(Continued)

*Primary Examiner* — Eric D. Bertram
(74) *Attorney, Agent, or Firm* — Schwegman Lundberg & Woessner, P.A.

(57) ABSTRACT

A method and apparatus for selecting neural stimulation electrode configuration is provided. One aspect of this disclosure relates to an implantable medical device including a neural stimulator adapted to generate neural stimulation signals and an electrode configuration tester for testing a first electrode configuration for stimulating a desired neural target. The device includes a controller to control the neural stimulator to selectively provide a first neural stimulation signal with appropriate signal characteristics to stimulate the desired neural target using the first electrical configuration and a second neural stimulation signal with appropriate signal characteristics to stimulate the desired neural target using a second electrode configuration, and adapted to communicate with the electrode configuration tester and to respond to an indication that an efficacy of the first electrode configuration is lower than a threshold by providing the neural stimulation using the second neural stimulation signal. Other aspects and embodiments are provided herein.

20 Claims, 7 Drawing Sheets

(51) Int. Cl.
  *A61N 1/362* (2006.01)
  *A61N 1/368* (2006.01)

(56) References Cited

U.S. PATENT DOCUMENTS

| | | | |
|---|---|---|---|
| 5,095,905 | A | 3/1992 | Klepinski |
| 5,251,634 | A | 10/1993 | Weinberg |
| 5,487,756 | A * | 1/1996 | Kallesoe et al. ............ 607/118 |
| 6,233,488 | B1 * | 5/2001 | Hess ............................ 607/58 |
| 6,272,377 | B1 * | 8/2001 | Sweeney et al. ............ 600/515 |
| 6,600,954 | B2 | 7/2003 | Cohen et al. |
| 6,600,956 | B2 | 7/2003 | Maschino et al. |
| 6,606,516 | B2 | 8/2003 | Levine |
| 6,658,294 | B1 | 12/2003 | Zadeh et al. |
| 2003/0176894 | A1 | 9/2003 | Stahmann et al. |
| 2003/0204223 | A1 | 10/2003 | Leinders et al. |
| 2004/0064161 | A1 | 4/2004 | Gunderson et al. |
| 2004/0158298 | A1 * | 8/2004 | Gliner et al. .................... 607/48 |
| 2006/0259078 | A1 | 11/2006 | Libbus |
| 2008/0177365 | A1 | 7/2008 | Bolea et al. |

FOREIGN PATENT DOCUMENTS

| | | |
|---|---|---|
| WO | WO-0158520 A1 | 8/2001 |
| WO | WO-2005028027 A1 | 3/2005 |
| WO | WO-2005028028 A1 | 3/2005 |
| WO | WO-2006124697 A1 | 11/2006 |

OTHER PUBLICATIONS

"U.S. Appl. No. 11/130,023, Final Office Action mailed Apr. 30, 2009", 9 pgs.

"U.S. Appl. No. 11/130,023, Final Office Action mailed Jun. 18, 2008", 10 pgs.

"U.S. Appl. No. 11/130,023, Non-Final Office Action mailed Oct. 3, 2008", 10 pgs.

"U.S. Appl. No. 11/130,023, Non-Final Office Action mailed Dec. 21, 2007", OARN, 8 pgs.

"U.S. Appl. No. 11/130,023, Response filed Aug. 25, 2009 to Final Office Action mailed Apr. 30, 2009", 13 pgs.

"U.S. Appl. No. 11/130,023, Response filed Jan. 22, 2009 to Non Final Office Action mailed Oct. 3, 2008", 12 pgs.

"U.S. Appl. No. 11/130,023, Response filed Mar. 20, 2008 to NOn-Final Office Action mailed Dec. 21, 2007", 10 pgs.

"U.S. Appl. No. 11/130,023, Response filed Sep. 15, 2008 to Final Office Action mailed Jun. 18, 2008", 11 pgs.

"U.S. Appl. No. 11/130,023, Restriction Requirement mailed Sep. 24, 2007", 7 pgs.

"U.S. Appl. No. 11/933,209, Preliminary Statement filed Oct. 31, 2007", 2 pgs.

"International Search Report and Written Opinion for Application No. PCT/US2006/018588, Date Mailed Oct. 5, 2006", 13 Pages.

"Japanese Application Serial No. 2008-512383, Office Action mailed Oct. 21, 2011", 7 pgs.

"Japanese Application Serial No. 2008-512383, Response filed Jan. 17, 2012 to Non Final Office Action dated Oct. 20, 2011", (w/ English Translation of Amended Claims), 15 pgs.

Nolan, J., et al., "Prospective Study of Heart Rate Variability and Mortality in Chronic Heart Failure: Results of the United Kingdom Heart Failure Evaluation and Assessment of Risk Trial (UK—Heart).", Circulation, 98(15), (1998), 1510-1516.

Sigurdsson, A., et al., "The Role of Neurohormonal Activation in Chronic Heart Failure and Postmyocardial Infarction", American Heart Journal, 132(1, Part 2), (Jul. 1996), 229-234.

"U.S. Appl. No. 11/130,023, Response filed Oct. 23, 2007 to Restriction Requirement mailed Sep. 24, 2007", 14 pgs.

* cited by examiner

METHOD AND APPARATUS FOR ELECTRONICALLY SWITCHING ELECTRODE CONFIGURATION

CLAIM OF PRIORITY

This application is a division of and claims the benefit of priority under 35 U.S.C. §120 to Imad Libbus, U.S. patent application Ser. No. 11/130,023, entitled "Method And Apparatus For Electronically Switching Electrode Configuration," filed on May 16, 2005, which is hereby incorporated by reference herein in its entirety.

TECHNICAL FIELD

This disclosure relates generally to implantable medical devices and, more particularly, to systems for electronically switching electrode configuration for neural stimulation leads.

BACKGROUND

Neural stimulation has been the subject of a number of studies and has been proposed for several therapies. The autonomic system controls physiological activities of the body and the imbalance of autonomic tone is related to many diseases and conditions. Reduced autonomic balance (increase in sympathetic and decrease in parasympathetic cardiac tone) during heart failure has been shown to be associated with left ventricular dysfunction and increased mortality. Sympathetic inhibition, as well as parasympathetic activation, have been associated with reduced arrhythmia vulnerability following a myocardial infarction. Vagus nerve stimulation has been proposed to treat sleep disorders, gastrointestinal motility, eating disorders, obesity, anorexia, gastrointestinal tract disorders, hypertension, coma, and epilepsy. Direct electrical stimulation of parasympathetic nerves can activate the baroreflex, inducing a reduction of sympathetic nerve activity and reducing blood pressure by decreasing vascular resistance. Direct stimulation of the vagal parasympathetic fibers has been shown to reduce heart rate via the sympathetic nervous system. In addition, some research indicates that chronic stimulation of the vagus nerve may be of protective myocardial benefit following cardiac ischemic insult.

Neural stimulation leads are designed to stimulate fragile neural tissue, and, when compared to conventional cardiac leads, are more susceptible to problems which affect current delivery. These include problems due to the fragility of the electrode, such as electrode fracture, anodization, and corrosion, changes in the electrode/nerve interface due to encapsulation or fibrosis, and in the case of intravascular leads, variability in the anatomic relationship between the vessel and the nerve.

SUMMARY

The above-mentioned problems and others not expressly discussed herein are addressed by the present subject matter and will be understood by reading and studying this specification.

Disclosed herein, among other things, is a method for electronically switching electrode configuration for neural stimulation leads. The method includes testing a first electrode configuration to deliver neural stimulation therapy. The method also includes comparing test results of the first electrode configuration to desired ranges of test results for the first electrode configuration. The method further includes selecting a second electrode configuration to deliver neural stimulation therapy if the test results for the first electrode configuration are not within the desired ranges. Test results include measured physiological parameters, in various embodiments. Test results include measured impedance for the first electrode configuration, in an embodiment. According to an embodiment, the impedance for the first electrode configuration is measured intermittently. According to an embodiment, the impedance for the first electrode configuration is measured periodically. According to an embodiment, the impedance for the first electrode configuration is measured in between deliveries of neural stimulation therapy.

One aspect of this disclosure relates to an implantable medical device for electronically switching electrode configuration for neural stimulation leads. According to one embodiment, the implantable medical device includes a neural stimulator adapted to generate neural stimulation signals and an electrode configuration tester for testing a first electrode configuration for stimulating a desired neural target. The implantable medical device further includes a controller to control the neural stimulator to selectively provide a first neural stimulation signal with appropriate signal characteristics to stimulate the desired neural target using the first electrical configuration and a second neural stimulation signal with appropriate signal characteristics to stimulate the desired neural target using a second electrode configuration, and adapted to communicate with the electrode configuration tester and to respond to an indication that an efficacy of the first electrode configuration is lower than a threshold by providing the neural stimulation using the second neural stimulation signal.

One aspect of this disclosure relates to a system for electronically selecting electrode configurations for neural stimulation therapy. The system includes at least one neural stimulation lead having a proximal portion and a distal portion and a plurality of electrodes along the distal portion of the at least one lead, with at least one of the plurality of electrodes forming part of a first electrode configuration to deliver neural stimulation therapy and another at least one of the plurality of electrodes forming part of a second electrode configuration to deliver neural stimulation therapy. The system also includes an implantable medical device coupled to the proximal portion of the at least one lead. According to this embodiment, the implantable device includes a neural stimulator and a controller to communicate with the neural stimulator, the controller being adapted to deliver an electrical signal to the first electrode configuration to deliver neural stimulation therapy, to measure impedance for the first electrode configuration, and to select the second electrode configuration if the measured impedance for the first electrode configuration is not within a desired range of impedance.

One aspect of this disclosure relates to a system for insuring the continuous delivery of neural stimulation therapy in the event of an electrode failure. The system includes a means for testing a first electrode configuration to deliver neural stimulation therapy, a means for comparing test results of the first electrode configuration to a desired range of results for the first electrode configuration, and a means for selecting a second electrode configuration to deliver neural stimulation therapy if the test results for the first electrode configuration are not within the desired range. According to one embodiment, the first and second electrode configurations are along a multipolar lead. According to another embodiment, the first and second electrode configurations are on at least two neural stimulation leads.

This Summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

DETAILED DESCRIPTION

Figure 1:
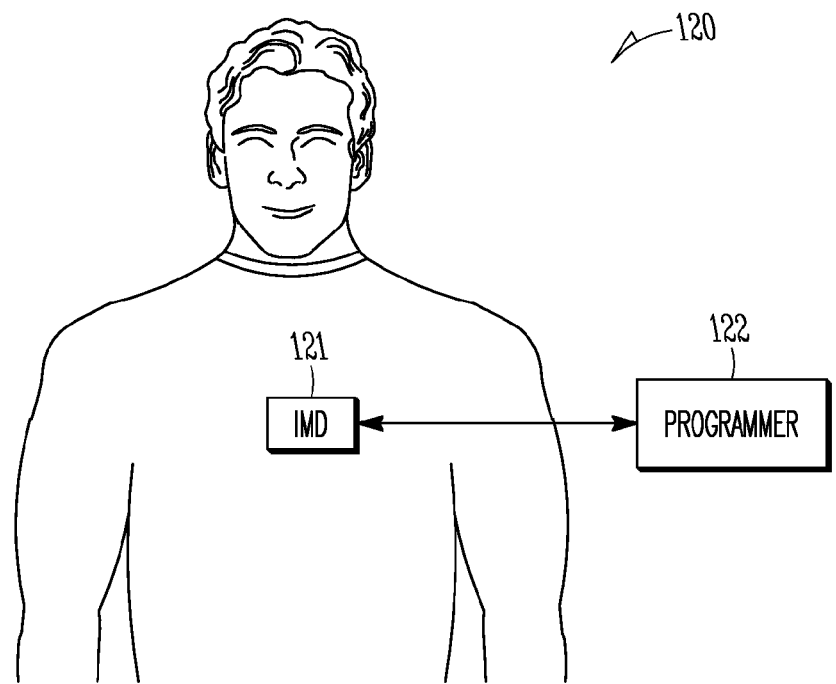
FIG. 1 illustrates a system including an implantable medical device (IMD) and a programmer, according to one embodiment.

The following detailed description refers to the accompanying drawings which show, by way of illustration, specific aspects and embodiments in which the present invention may be practiced. The various embodiments are not necessarily mutually exclusive, as aspects of one embodiment can be combined with aspects of another embodiment. These embodiments are described in sufficient detail to enable those skilled in the art to practice the invention. Other embodiments may be utilized and structural, logical, and electrical changes may be made without departing from the scope of the present invention.

A brief discussion of the physiology related to neurology is provided to assist the reader with understanding this disclosure. The automatic nervous system (ANS) regulates "involuntary" organs. The ANS includes the sympathetic nervous system and the parasympathetic nervous system. The sympathetic nervous system is affiliated with stress and the "fight or flight response" to emergencies. The parasympathetic nervous system is affiliated with relaxation and the "rest and digest response." The ANS maintains normal internal function and works with the somatic nervous system. Autonomic balance reflects the relationship between parasympathetic and sympathetic activity. A change in autonomic balance is reflected in changes in heart rate, heart rhythm, contractility, remodeling, inflammation and blood pressure. Changes in autonomic balance can also be seen in other physiological changes, such as changes in abdominal pain, appetite, stamina, emotions, personality, muscle tone, sleep, and allergies, for example.

An example of neural stimulation is baroreflex stimulation. Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity, stimulates the parasympathetic nervous system and reduces systemic arterial pressure by decreasing peripheral vascular resistance and cardiac contractility. Baroreceptors are naturally stimulated by internal pressure and the stretching of vessel wall (e.g. arterial wall). Neural stimulation of other neural targets is within the scope of the present disclosure, including stimulation of efferent and afferent pathways for parasympathetic and sympathetic nerves.

A neural stimulation lead is a lead for delivering neural stimulation therapy, and can be placed in a number of appropriate locations. For example, various lead embodiments to stimulate a baroreflex are expandable, and are adapted to be placed in the pulmonary artery in the proximity of a high concentration of baroreceptors. Various lead embodiments are adapted to stimulate nerve endings in cardiac fat pads. Some lead embodiments are transvascular leads placed proximal to a cardiac fat pad. Some lead embodiments place an epicardial lead in a cardiac fat pad. Various lead embodiments include a cuff electrode adapted to be placed around a nerve, such as the aortic, carotid or vagus nerve. A nerve cuff refers to any lead configuration that is placed around a nerve trunk, including configurations placed around a sheath containing a nerve trunk. Some lead embodiments include a transvascular lead placed proximal to a nerve, such as the vagus, aortic, or carotid nerve. Other leads can be placed in other neural stimulation and neural sensing locations to perform baroreflex or other therapy.

Neural stimulation leads are designed to stimulate fragile neural tissue and are susceptible to problems which affect current delivery. These include problems due to the fragility of the electrode, such as electrode fracture, anodization, and corrosion, changes in the electrode/nerve interface due to encapsulation or fibrosis, and in the case of intravascular leads, variability in the anatomic relationship between the vessel and the nerve. Due to the problems associated with neural stimulation leads, improved systems and methods are needed to ensure uninterrupted chronic neural stimulation without the need for invasive lead replacement.

The present system is capable of electronically selecting between a plurality of electrode configurations, insuring the continuous delivery of neural stimulation therapy in the event of an electrode failure. An embodiment of the system measures electrode impedance and selects alternative electrode configurations to deliver neural stimulation therapy if impedance deviates from a desired range. By avoiding common problems associated with fragile neural stimulation leads and electrodes, this system facilitates therapies for post-myocardial infarction or heart failure patients such as anti-remodeling therapy through neural stimulation, therapies for patients with other cardiovascular conditions such as hypertension or syncope, or therapies for patients with non-cardiovascular conditions such as epilepsy, obesity or dysautonomia. In addition, this system increases the reliability and reduces the overall implantation time for various neural stimulation devices.

Implantable Medical Devices

FIG. 1 illustrates a system 120 including an implantable medical device (IMD) 121 and a programmer 122, according to one embodiment. Various embodiments of the IMD 121 include neural stimulator functions only, and various embodiments include a combination of neural stimulation and cardiac rhythm management functions. The programmer 122 and the IMD 121 are capable of wirelessly communicating data and instructions. In various embodiments, for example, the programmer 122 and IMD 121 use telemetry coils to wirelessly communicate data and instructions. Thus, the programmer can be used to adjust the programmed therapy provided by the IMD 121, and the IMD can report device data (such as battery and lead resistance) and therapy data (such as sense and stimulation data) to the programmer using radio telemetry, for example. According to various embodiments, the IMD 121 is adapted for electronically switching electrode configuration for neural stimulation leads using the method disclosed in FIG. 7 below. According to various embodiments, the IMD 121 includes a sensor to sense ANS activity. Such a sensor can be used to perform feedback in a closed loop control system. For example, various embodiments sense surrogate parameters, such as respiration and blood pressure, indicative of ANS activity. According to various embodiments, the IMD further includes cardiac stimulation capabilities, such as pacing and defibrillating capabilities in addition to the capabilities to stimulate nerve bundles and/or sense ANS activity.

Figure 2:
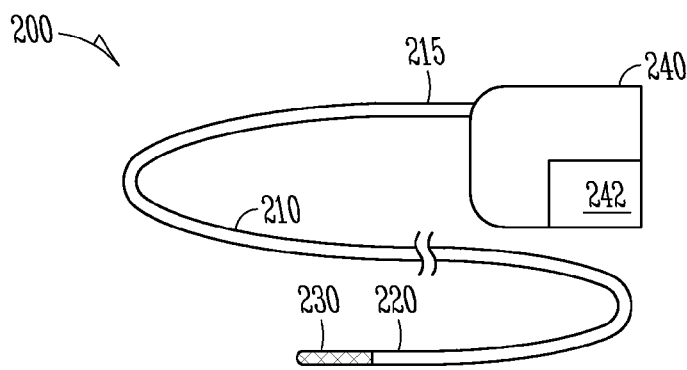
FIG. 2 illustrates a neural stimulation lead and an implantable medical device (IMD), according to one embodiment.

FIG. 2 illustrates a neural stimulation lead and an implantable medical device (IMD), according to one embodiment. Neural stimulation lead 200 includes a flexible lead body 210 extending from a proximal end 215 to a distal end 220. A plurality of electrodes 230 are proximate the distal end 220 of lead body 210. According to various embodiments, the electrodes are part of a nerve cuff for direct neural stimulation. The cuff electrode is placed around the vagus nerve in one embodiment, and around the carotid or aortic nerve in other embodiments. According to further embodiments, the electrodes are adapted to be chronically implanted in a blood vessel adjacent a nerve trunk for providing stimulation transvascularly to a nerve trunk, through the wall of the adjacent blood vessel. Other types of electrodes that are adapted to stimulate a neural target are within the scope of this disclosure.

Neural stimulation lead 200 is coupled to an implantable medical device (IMD) 240, or pulse generator. Neural stimulation lead 200 includes conductors, such as coiled conductors that electrically couple pulse generator 240 to electrodes 230. Accordingly, implantable medical device 240 can deliver a stimulation signal via the electrodes 230. The lead further includes outer insulation to insulate the conductor. The system can include a unipolar system with the case acting as an electrode or a bipolar system with a pulse between two distally located electrodes. In other embodiments, the lead can include a multipolar system.

In one embodiment, implantable medical device 240 includes hardware, circuitry and software to perform neural stimulation functions, and includes controller circuitry 242. The controller circuitry 242 is capable of being implemented using hardware, software, and combinations of hardware and software. For example, according to various embodiments, the controller circuitry 242 includes a processor to perform instructions embedded in a memory to perform functions associated with neural stimulation, including electronically switching electrode configuration.

System for Electronically Switching Electrode Configuration

Figure 3:
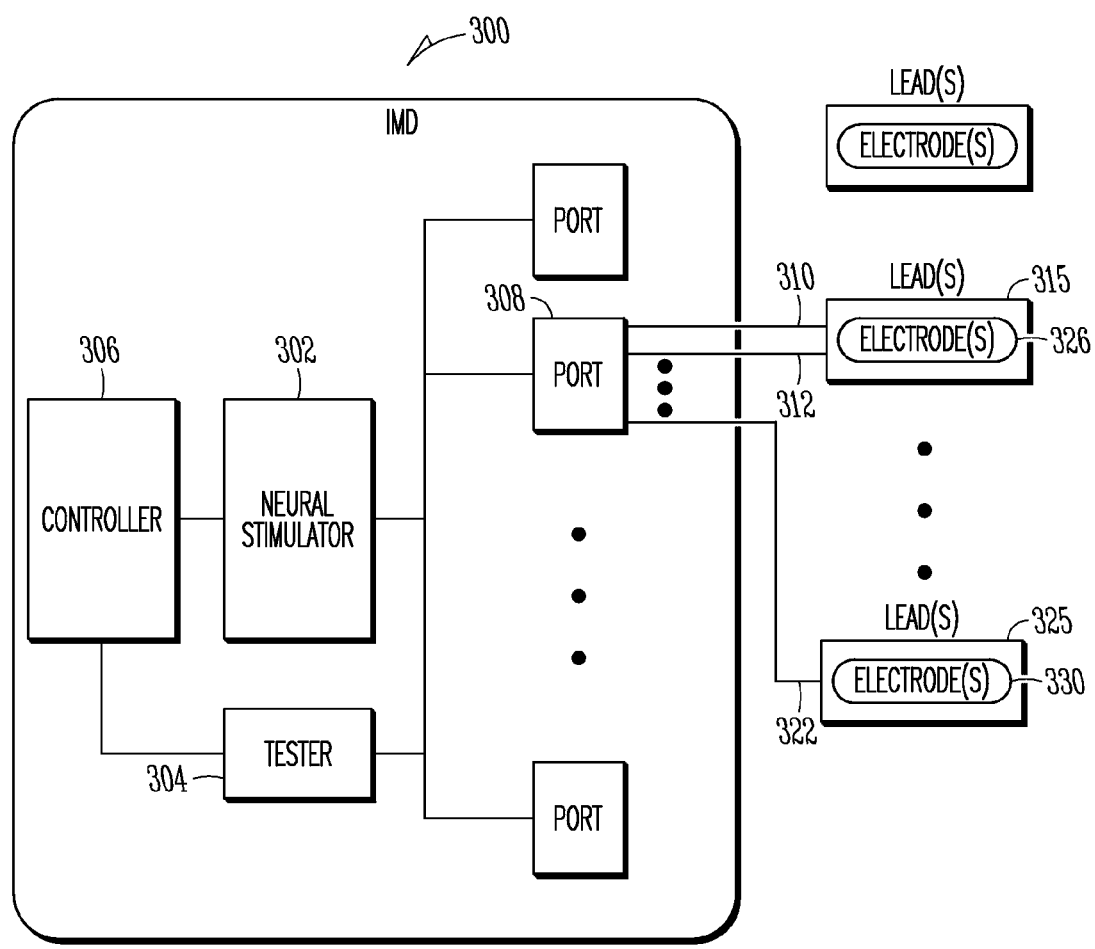
FIG. 3 illustrates an apparatus for electronically switching electrode configuration for neural stimulation therapy, according to one embodiment.

FIG. 3 illustrates an apparatus for electronically switching electrode configuration for neural stimulation therapy, according to one embodiment. An implantable medical device 300 includes a neural stimulator 302 adapted to generate neural stimulation signals, an electrode configuration tester 304 for testing a first electrode configuration for stimulating a desired neural target, and a controller 306 to control the neural stimulator 302 to selectively provide a first neural stimulation signal with appropriate signal characteristics to stimulate the desired neural target using the first electrode configuration and a second neural stimulation signal with appropriate signal characteristics to stimulate the desired neural target using a second electrode configuration, and adapted to communicate with the electrode configuration tester 304 and to respond to an indication that an efficacy of the first electrode configuration is lower than a threshold by providing the neural stimulation using the second neural stimulation signal. Electrode channels 310 and 312 are shown connected to the device 300 via at least one port 308, and connected to electrodes 320 via at least one lead 315. In various embodiments, electrode configurations can include electrodes 330 on separate leads 325 connected to the device 300 via additional channels 322. Thus, the first and second electrode configurations to deliver neural stimulation therapy are on a single lead in one embodiment, and are on at least two leads in another embodiment.

According to various embodiments, the first and second stimulation signals have the same signal characteristics. According to other embodiments, the first and second stimulation signals have different signal characteristics. Signal characteristics include amplitude, frequency, burst frequency and pulse width. One or more of these characteristics can be adjusted by the controller.

The channels are grouped into first and second channel sets in one embodiment. The first and second channels sets include exclusive channels where no electrodes are shared between the channels, shared channels where some electrodes are shared between channels, or different number of channels where fewer or more electrodes are used in the first and second electrode configurations. In an embodiment, the first and second electrode configurations are multipolar. In an embodiment, the first and second electrode configurations are bipolar. In an embodiment, the first and second electrode configurations are unipolar. The electrode configurations may include electrodes along an intravascular lead to transvascularly stimulate neural target in one embodiment, or along a nerve cuff electrode in a further embodiment. In one embodiment, the electrode configuration tester 304 includes an impedance measurement circuit to measure impedance for the first electrode configuration, compare the measured impedance to a desired impedance range for the first electrode configuration, and determine that an efficacy of the first electrode configuration is below a threshold when the measured impedance is not within the desired range.

Figure 4:
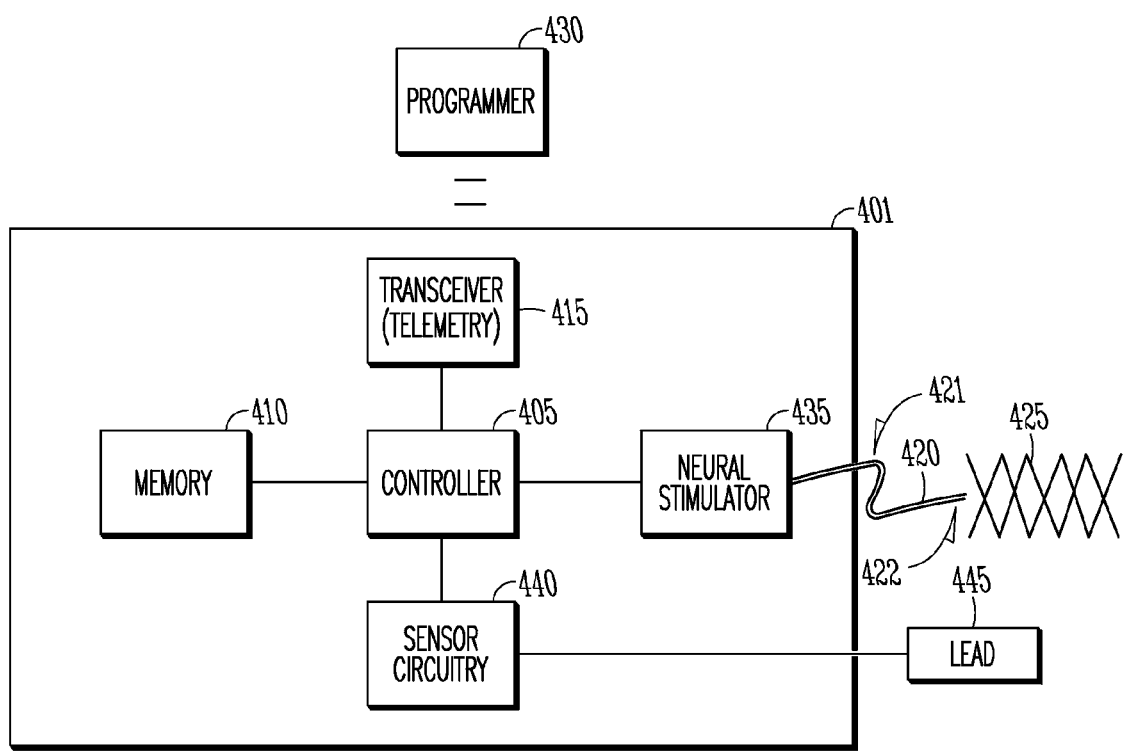
FIG. 4 is a schematic illustration of an implantable system for delivering neural stimulation and electronically selecting electrode configurations, according to one embodiment.

FIG. 4 is a schematic illustration of an implantable system for delivering neural stimulation and electronically selecting electrode configurations, according to one embodiment. The system includes at least one neural stimulation lead 420 having a proximal portion 421 and a distal portion 422. The system also includes a plurality of electrodes 425 along the distal portion 422 of the at least one lead, with at least one of the plurality of electrodes forming part of a first electrode configuration to deliver neural stimulation therapy and another at least one of the plurality of electrodes forming part of a second electrode configuration to deliver neural stimulation therapy. The system also includes an implantable medical device 401, coupled to the proximal portion 421 of the at least one lead 420. The implantable device 401 includes a neural stimulator 435 and a controller 405 to communicate with the neural stimulator, the controller being adapted to deliver an electrical signal to the first electrode configuration to deliver neural stimulation therapy, to measure impedance for the first electrode configuration, and to select the second electrode configuration if the measured impedance for the first electrode configuration is not within a desired range of impedance.

According to additional embodiments, the implantable medical device 401 includes a telemetry circuit 415 to communicate with the controller 405 and an external module, programmer 430. According to further embodiments, the system also includes a memory circuit 410 to communicate with the controller 405, the memory having embedded computer-readable instructions which are operable on by the controller. In addition, the memory can store measured electrode configurations and characteristics, such as impedance, for trending over time, which can be incorporated into an Advanced Patient Management (APM) system in one embodiment.

The at least one neural stimulation lead 420 includes a direct stimulation lead for providing stimulation directly to a nerve trunk, according to one embodiment. An example of a direct stimulation lead includes a lead with a nerve cuff. In other embodiments, the at least one neural stimulation lead 420 includes an indirect stimulation lead for providing stimulation indirectly to a nerve trunk, through the wall of an adjacent blood vessel. Examples of indirect stimulation leads include chronically implanted transvascular neural stimulation leads.

The illustrated system also includes optional sensor circuitry 440 that is coupled to a lead 445. The controller circuit 405 processes sensor data from the sensor circuitry and delivers a therapy responsive to the sensor data.

Combined Neural Simulation and Cardiac Rhythm Management

Figure 5:
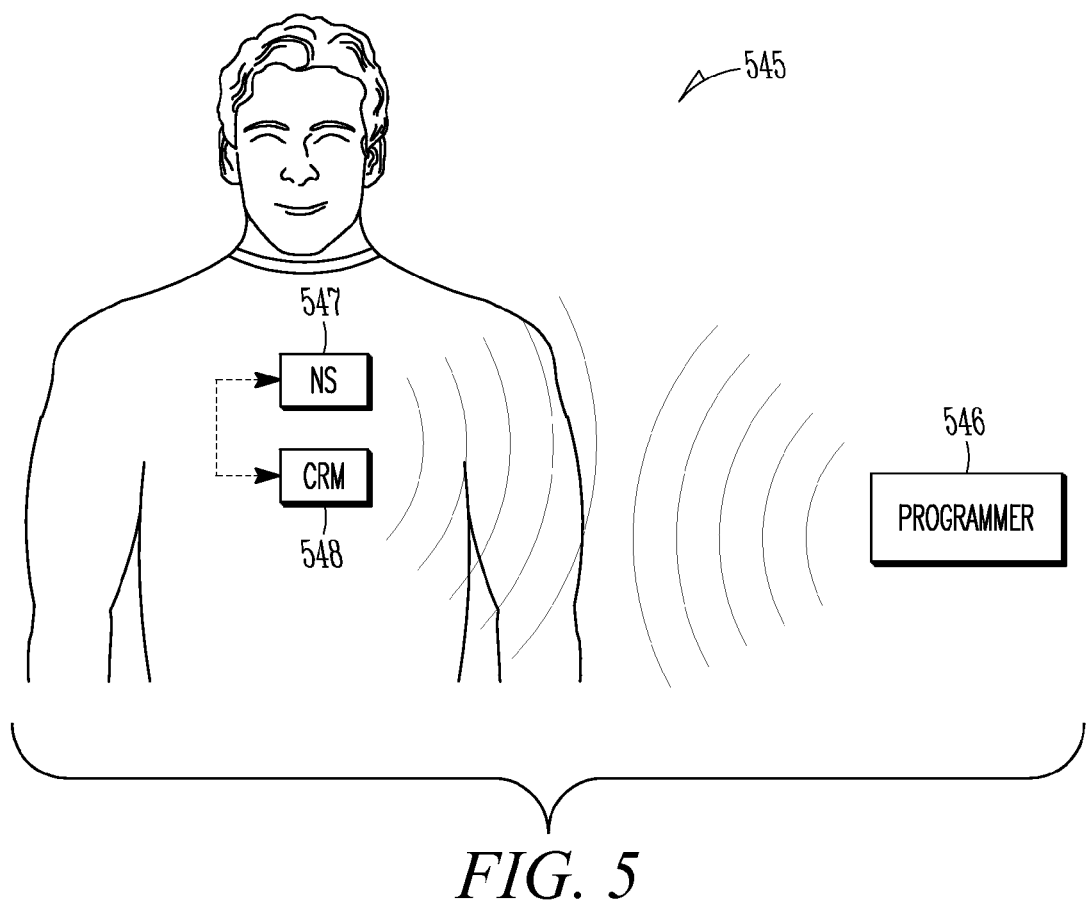
FIG. 5 illustrates a system including neural stimulation and cardiac rhythm management therapy, according to one embodiment.

FIG. 5 illustrates a system including neural stimulation and cardiac rhythm management therapy, according to one embodiment. The system 545 includes a programmer 546, an implantable neural stimulator (NS) device 547 and an implantable cardiac rhythm management (CRM) device 548, according to various embodiments of the present subject matter.

Various embodiments of the present subject matter include stand-alone implantable NS systems, and include implantable devices that have integrated NS and CRM components, and further include systems with at least one implantable NS device and an implantable CRM device capable of communicating with each other. Some embodiments of the NS and CRM devices directly communicate with each other wirelessly, some embodiments communicate through a wire lead connecting the implantable devices, and some embodiments independently communicate with an external device that functions as an intermediary to provide communication between the NS and CRM devices. Although implantable systems are illustrated and discussed, various aspects and embodiments of the present subject matter can be implemented in external devices.

Examples of CRM devices include implantable pacemakers, implantable cardiac defibrillators (ICDs), implantable devices capable of performing pacing and defibrillating functions, and CRT devices. Implantable CRM devices provide electrical stimulation to selected chambers of the heart in order to treat disorders of cardiac rhythm. An implantable pacemaker, for example, is a CRM device that paces the heart with timed pacing pulses. The pacing pulses can be timed from other pacing pulses or sensed electrical activity. If functioning properly, the pacemaker makes up for the heart's inability to pace itself at an appropriate rhythm in order to meet metabolic demand by enforcing a minimum heart rate. Some CRM devices synchronize pacing pulses delivered to different areas of the heart in order to coordinate the contractions. Coordinated contractions allow the heart to pump efficiently while providing sufficient cardiac output. Some embodiments provide neural stimulation to treat hypertension. CRM functions can be improved by sensing neural activity to provide an input or feedback for the CRM functions. For example, various embodiments record the nerve activity in the cardiac fat pads and use the sensed nerve activity to control the CRM functions. In another example, various embodiments sense AV node activity to determine an intrinsic AV delay, allowing the CRM device to use the determined intrinsic AV delay to appropriately time pacing pulses.

Figure 6:
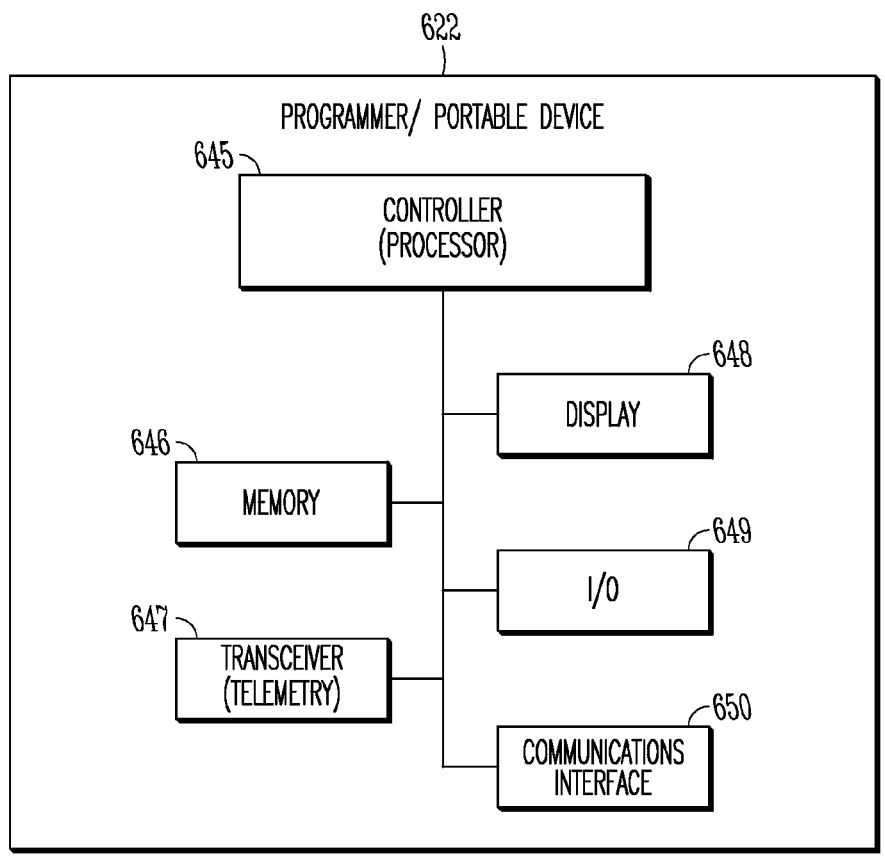
FIG. 6 illustrates a programmer such as illustrated in the system of FIG. 1 or FIG. 4 or other external device to communicate with the implantable medical device(s), according to one embodiment.

FIG. 6 illustrates a programmer 622 such as illustrated in the system of FIG. 1 or FIG. 4 or other external device to communicate with the implantable medical device(s), according to one embodiment. An example of another external device includes Personal Digital Assistants (PDAs) or personal laptop and desktop computers in an Advanced Patient Management (APM) system. The illustrated device 622 includes controller circuitry 645 and a memory 646. The controller circuitry 645 is capable of being implemented using hardware, software, and combinations of hardware and software. For example, according to various embodiments, the controller circuitry 645 includes a processor to perform instructions embedded in the memory 646 to perform a number of functions, including communicating data and/or programming instructions to the implantable devices. The illustrated device 622 further includes a transceiver 647 and associated circuitry for use to communicate with an implantable device. Various embodiments have wireless communication capabilities. For example, various embodiments of the transceiver 647 and associated circuitry include a telemetry coil for use to wirelessly communicate with an implantable device. The illustrated device 622 further includes a display 648, input/output (I/O) devices 649 such as a keyboard or mouse/pointer, and a communications interface 650 for use to communicate with other devices, such as over a communication network. According to an embodiment, the programmer provides the user option of disabling automatic scanning of electrode configurations. The programmer also provides the user option of manually initiating an electrode configuration scan, according to an embodiment.

Method for Electronically Switching Electrode Configuration

Figure 7:
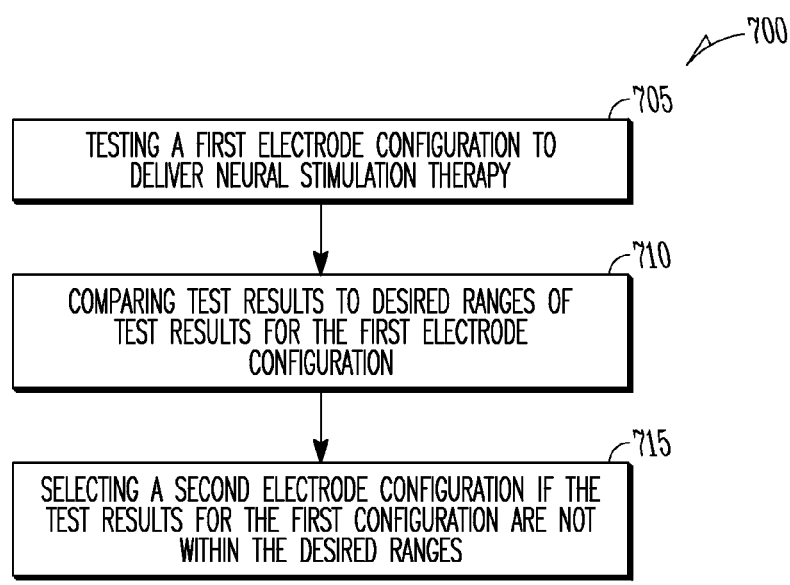
FIG. 7 illustrates a flow diagram of a method for electronically switching electrode configuration for neural stimulation leads, according to one embodiment.

FIG. 7 illustrates a flow diagram of a method for electronically switching electrode configuration for neural stimulation leads, according to one embodiment. The method 700 includes testing a first electrode configuration to deliver neural stimulation therapy, at 705. Other embodiments use various methods to determine the ability of the electrode configuration to stimulate a nerve target. The method also includes comparing test results of the first electrode configuration to desired ranges of test results for the first electrode configuration, at 710. The method further includes selecting a second electrode configuration to deliver neural stimulation therapy if the test results for the first electrode configuration are not within the desired ranges, at 715. According to various embodiments, the test results include a measured physiological response. As an example, a multipolar electrode is placed in the vicinity of a nerve target, and different electrode configurations are selected to elicit a desired response. The desired response may include the largest appropriate physiological response, the smallest inappropriate physiological response (or side effect), or some combination of the two, in various embodiments. Examples of physiological responses include changes in heart rate, blood pressure, and respiration. Testing of other physiological responses is within the scope of this disclosure.

According to an embodiment, the test results include measured impedance of the first electrode configuration. According to one embodiment, the impedance for the first electrode configuration is measured intermittently. According to another embodiment, the impedance for the first electrode configuration is measured periodically. According to a further embodiment, the impedance for the first electrode configuration is measured in between deliveries of neural stimulation therapy.

According to various embodiments, selecting a second electrode configuration to deliver neural stimulation therapy if the measured impedance for the first electrode configuration is not within the desired range includes measuring an impedance for the second electrode configuration to deliver neural stimulation therapy, and comparing the measured impedance of the second electrode configuration to a desired impedance range for the second electrode configuration. This is to ensure that second electrode configuration, which is selected when the first electrode configuration has impedance outside the desired range, has impedance within its desired range. In various embodiments, the first and second electrode configurations to deliver neural stimulation therapy are on a multipolar lead. In other embodiments, the first and second electrode configurations to deliver neural stimulation therapy are on at least two leads.

According to various embodiments, selecting a second electrode configuration to deliver neural stimulation therapy if the measured impedance for the first electrode configuration is not within the desired range includes disabling the first electrode configuration and enabling the second electrode configuration. According to further embodiments, neural stimulation therapy is then delivered via the second electrode configuration. In one embodiment, the method then measures an impedance for the second electrode configuration, compares the measured impedance of the second electrode configuration to a desired impedance range for the second electrode configuration, and selects a third electrode configuration to deliver neural stimulation therapy if the measured impedance for the second electrode configuration is not within the desired range for the second electrode configuration. In this manner, the method continues measuring impedance for the currently selected electrode configuration, and if its impedance deviates from a desired range, a different, compliant configuration is selected.

According to an embodiment, a multipolar expandable electrode is placed using the disclosed system. In this embodiment, the electrode is implanted near the desired target, and the user or programmer initiates an electrode configuration test. The test results for each possible configuration are compared, and the configuration with the most favorable (and/or least unfavorable) physiological response is selected. Accuracy and ease of electrode implantation are enhanced in this manner.

Electrode Configurations

FIGS. 8A through 8E are illustrations of electrode configurations used by the present system, according to various embodiments. In the embodiment illustrated in FIG. 8A, a first electrode configuration 801 is used to deliver neural stimulation by generating an electrical signal from electrode A to electrode B. In this embodiment, if an efficacy of the first electrode configuration is lower than a threshold, the system switches to a second electrode configuration 803 to deliver neural stimulation by generating an electrical signal from electrode C to electrode D. Electrodes A, B, C and D may be connected to the same neural stimulation lead or to different neural stimulation leads in various embodiments.

Figure 8A:
FIGS. 8A through 8E are illustrations of electrode configurations used by the present system, according to various embodiments.
Figure 8B:
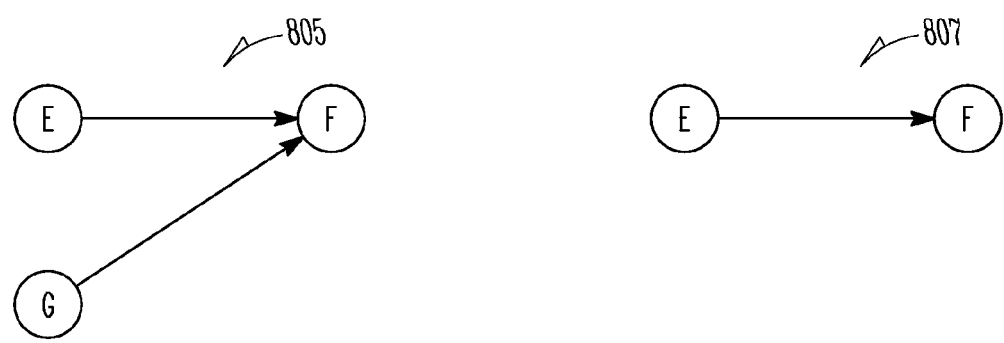

In the embodiment illustrated in FIG. 8B, a first electrode configuration 805 is used to deliver neural stimulation by generating an electrical signal from electrode E to electrode F and from electrode G to electrode F. In this embodiment, if an efficacy of the first electrode configuration is lower than a threshold, the system switches to a second electrode configuration 807 by removing an electrode (here electrode G) to deliver neural stimulation by generating an electrical signal from electrode E to electrode F. Electrodes E, F and G may be connected to the same neural stimulation lead or to different neural stimulation leads in various embodiments.

Figure 8C:
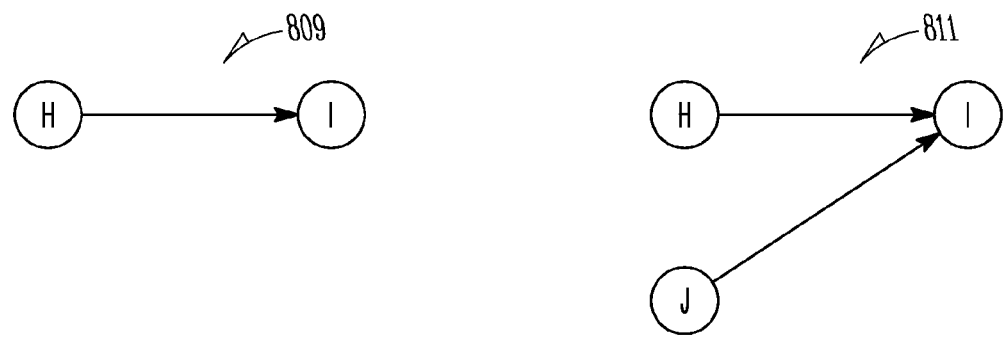

In the embodiment illustrated in FIG. 8C, a first electrode configuration 809 is used to deliver neural stimulation by generating an electrical signal from electrode H to electrode I. In this embodiment, if an efficacy of the first electrode configuration is lower than a threshold, the system switches to a second electrode configuration 811 by adding an electrode (here electrode J) to deliver neural stimulation by generating an electrical signal from electrode H to electrode I and from electrode J to electrode I. Electrodes H, I and J may be connected to the same neural stimulation lead or to different neural stimulation leads in various embodiments.

Figure 8D:

In the embodiment illustrated in FIG. 8D, a first electrode configuration 813 is used to deliver neural stimulation by generating an electrical signal from electrode K to electrode L. In this embodiment, if an efficacy of the first electrode configuration is lower than a threshold, the system switches to a second electrode configuration 815 by generating an electrical signal from electrode K to electrode M. Electrodes K, L and M may be connected to the same neural stimulation lead or to different neural stimulation leads in various embodiments.

Figure 8E:

In the embodiment illustrated in FIG. 8E, a first electrode configuration 817 is used to deliver neural stimulation by generating an electrical signal from electrode N to electrode P. In this embodiment, if an efficacy of the first electrode configuration is lower than a threshold, the system switches to a second electrode configuration 819 by generating an electrical signal from electrode O to electrode P. Electrodes N, O and P may be connected to the same neural stimulation lead or to different neural stimulation leads in various embodiments. Other embodiments of electrode configurations that are adapted to stimulate a neural target are within the scope of this disclosure. In various embodiments, switching electrode configuration changes stimulation from bipolar to unipolar. In various embodiments, switching electrode configuration changes stimulation from unipolar to bipolar.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. An implantable medical device, comprising:
   a neural stimulator adapted to provide neural stimulation therapy using either a first electrode configuration to deliver neural stimulation or a second electrode configuration to deliver neural stimulation;
   a controller operably connected to the neural stimulator and configured to select the first electrode configuration to control delivery of the neural stimulation therapy through the first electrode configuration;
   an electrode configuration tester for testing for a fault in the first electrode configuration during delivery of the neural stimulation therapy to a patient, the fault occurring when the efficacy of the neural stimulation therapy using the first electrode configuration is lower than a threshold; and
   the controller operably connected to the electrode configuration tester to repeatedly test the first electrode configuration during delivery of the neural stimulation therapy to ensure uninterrupted neural stimulation to the patient, and to respond to a detected failure in the first electrode configuration by selecting the second electrode configuration and controlling delivery of the neural stimulation therapy through the second electrode configuration.

2. The implantable medical device of claim 1, wherein the first and second stimulation signals have same signal characteristics.

3. The implantable medical device of claim 1, wherein the first and second stimulation signals have different signal characteristics.

4. The implantable medical device of claim 1, wherein the first electrode configuration is unipolar.

5. The implantable medical device of claim 1, wherein the first electrode configuration is bipolar.

6. The implantable medical device of claim 1, wherein the first electrode configuration is multipolar.

7. The implantable medical device of claim 1, wherein the first electrode configuration includes an intravascular electrode to transvascularly stimulate the neural target.

8. The implantable medical device of claim 1, wherein the first electrode configuration includes a nerve cuff electrode.

9. The implantable medical device of claim 1, wherein the electrode configuration tester includes an impedance measurement circuit to measure impedance for the first electrode configuration, compare the measured impedance to a desired impedance range for the first electrode configuration, and determine that the efficacy of the first electrode configuration is below a threshold when the measured impedance is not within the desired range.

10. The implantable medical device of claim 1, wherein the electrode configuration tester is adapted to measure physiological response for the first electrode configuration, compare the measured physiological response to a desired range for the physiological response, and determine that the efficacy of the first electrode configuration is below a threshold when the measured physiological response is not within the desired range.

11. The implantable medical device of claim 1, further comprising:
    at least one neural stimulation lead having a proximal portion and a distal portion;
    a plurality of electrodes along the distal portion of the at least one lead, with at least one of the plurality of electrodes forming part of the first electrode configuration to deliver neural stimulation therapy and another at least one of the plurality of electrodes forming part of the second electrode configuration to deliver neural stimulation therapy; and
    wherein a portion of the implantable medical device is coup led to the proximal portion of the at least one lead.

12. The implantable medical device of claim 11, further comprising:
    a telemetry circuit to communicate with the controller and an external module.

13. The implantable medical device of claim 11, further comprising:
    a memory circuit to communicate with the controller; and
    computer-readable instructions embedded in the memory circuit, the computer-readable instructions being operable on by the controller to control delivery of neural stimulation therapy.

14. The implantable medical device of claim 13, wherein the at least one neural stimulation lead includes a nerve cuff.

15. The implantable medical device of claim 13, wherein the memory circuit is adapted to store measured impedance at different times for a time period to enable trending of the measured impedance.

16. The implantable medical device of claim 11, wherein the at least one neural stimulation lead includes a direct stimulation lead for providing stimulation directly to a nerve trunk.

17. The implantable medical device of claim 11, wherein the at least one neural stimulation lead includes an indirect stimulation lead for providing stimulation indirectly to a nerve trunk, through the wall of an adjacent blood vessel.

18. The implantable medical device of claim 11, further comprising a second lead having at least one additional electrode configuration.

19. The implantable medical device of claim 11, wherein the controller is configured to measure impedance for the first electrode configuration periodically.

20. The implantable medical device of claim 11, wherein the controller is configured to measure the impedance for the first electrode configuration in between deliveries of neural stimulation therapy.

* * * * *